(12) United States Patent
Majeed et al.

(10) Patent No.: US 11,299,706 B2
(45) Date of Patent: Apr. 12, 2022

(54) MICROBIAL BIOCONVERSION OF CURCUMINOIDS TO CALEBIN-A

(71) Applicants: Muhammed Majeed, Bangalore (IN); Kalyanam Nagabhushanam, East Windsor, NJ (US); Anju Majeed, East Windsor, NJ (US); Nooruddin Thajuddin, Tiruchirapalli (IN); Sivakumar Arumugam, Bangalore (IN); Krishnamurthy Kulithalai Viswanathan, Bangalore (IN); Samuel Thomas Manoharan, Bangalore (IN); Furqan Ali, Bangalore (IN); John Adams Sebastian, Bangalore (IN); Jamsheeda Moothedath, Bangalore (IN); Muthuraman Gnanamani, Bangalore (IN); Kirankumar Beede, Bangalore (IN)

(72) Inventors: Muhammed Majeed, Bangalore (IN); Kalyanam Nagabhushanam, East Windsor, NJ (US); Anju Majeed, East Windsor, NJ (US); Nooruddin Thajuddin, Tiruchirapalli (IN); Sivakumar Arumugam, Bangalore (IN); Krishnamurthy Kulithalai Viswanathan, Bangalore (IN); Samuel Thomas Manoharan, Bangalore (IN); Furqan Ali, Bangalore (IN); John Adams Sebastian, Bangalore (IN); Jamsheeda Moothedath, Bangalore (IN); Muthuraman Gnanamani, Bangalore (IN); Kirankumar Beede, Bangalore (IN)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 154 days.

(21) Appl. No.: 16/281,120

(22) Filed: Feb. 21, 2019

(65) Prior Publication Data

US 2019/0264295 A1    Aug. 29, 2019

(30) Foreign Application Priority Data

Feb. 23, 2018 (IN) .............................. 201841006854

(51) Int. Cl.
| | | |
|---|---|---|
| *C12N 1/14* | (2006.01) | |
| *C12N 1/20* | (2006.01) | |
| *A61K 36/9066* | (2006.01) | |
| *A61K 31/216* | (2006.01) | |
| *C12R 1/645* | (2006.01) | |
| *C12R 1/38* | (2006.01) | |

(52) U.S. Cl.
CPC ............ *C12N 1/145* (2021.05); *A61K 31/216* (2013.01); *A61K 36/9066* (2013.01); *C12N 1/205* (2021.05); *C12R 2001/38* (2021.05); *C12R 2001/645* (2021.05)

(58) Field of Classification Search
None
See application file for complete search history.

(56) References Cited

U.S. PATENT DOCUMENTS

2016/0002141 A1*   1/2016   Majeed .................. C07C 67/11
                                                                560/75

OTHER PUBLICATIONS

Xu et al., "Fungal endophytes from Dioscorea zingiberensis rhizomes and their antibacterial activity", Letters in Applied Microbiology 2008, vol. 46, pp. 68-72 (Year: 2008).*

* cited by examiner

Primary Examiner — Michelle F. Paguio Frising

(57) ABSTRACT

The present invention discloses a novel endophytic fungi, *Ovatospora brasiliensis* MTCC 25236 for the bioconversion of curcuminoids to Calebin-A and a method for its isolation from the rhizomes of *Curcuma* sp. The invention also discloses a method for the bioconversion of curcuminoids to Calebin-A using an endophytic fungi *Ovatospora brasiliensis* MTCC 25236 and bacterial species, *Acinetobacter johnsonii* and *Pseudomonas putida*.

4 Claims, 9 Drawing Sheets

Specification includes a Sequence Listing.

(A)            (B)            (C)

MICROBIAL BIOCONVERSION OF CURCUMINOIDS TO CALEBIN-A

CROSS-REFERENCE TO RELATED APPLICATION

The present application is a conventional application claiming priority from Indian provisional application no. IN 201841006854, filed on 23 Feb. 2018.

SEQUENCE INFORMATION

The present application contains a sequence listing which was filed electronically in ASCII format on Feb. 19, 2019, which is named Microbial_bioconversion-Sequence_listing_ST25.txt and 1,827 bytes in size. The provided sequence listing is incorporated by reference in its entirety.

BACKGROUND OF THE INVENTION

Field of the Invention

The invention in general pertains to microbial bioconversion of plant metabolites. Specifically, the invention relates to microbial bioconversion of curcuminoids, isolated from the rhizomes of *Curcuma caesia* to Calebin-A using fungal and bacterial sources.

Description of Prior Art

Turmeric (*Curcuma* Sp.) has long been used in the ancient Ayurvedic system of medicine for treating various ailments. It possesses many active metabolites viz curcumin, demethoxycurcumin, bisdemethoxycurcumin, ar-turmerone, curlone etc which is responsible for its biological function. Owing to their therapeutic potential, curcuminoids are widely used as dietary supplements. Recently, another molecule from the rhizome of *Curcuma* sp., identified as Calebin-A was reported to possess excellent therapeutic properties.

Chemically, Calebin-A and curcumin are very different. The differences are set forth below:
1. Calebin-A (STR #1) is an ester-ketone whereas Curcumin (SRT #2) is a diketone, more precisely a 1,3-diketone.
2. Curcumin structure has highly conjugated extended double bonds imparting a fluorescent characteristic yellow color that Calebin-A does not have. In fact, Calebin has only very light color because of their highly different structures.
3. Curcumin 1,3-diketonic structure brings about a keto-enol tautomerism. Curcumin exists nearly totally enolic in solution with a small amount of diketone in equilibrium with enolic form. Calebin-A does not all exhibit any keto-enol tautomerism.
4. Because of the keto-enol, a characteristic intra-molecular hydrogen bonded structure dominates the solid state structure of curcumin.
5. Curcumin is highly unstable in alkaline medium whereas Calebin-A is stable enough to form a sodium salt. Whereas Curcumin does degrade very quickly in higher pH >8, Calebin-A does not.
6. Curcumin is symmetric whereas Calebin-A is not symmetric in structure.
7. Curcumin forms metallic complexes whereas Calebin-A is not known to form such complexes.

Thus, due to the above differences, biological activity of curcumin and calebin-A will not be the same.

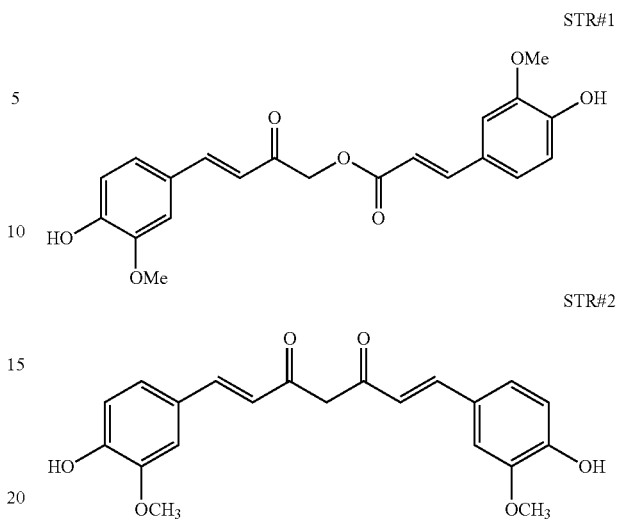

Calebin-A was reported to protect neuronal cells from amyloid-β insult (Park and Kim. Discovery of natural products from *Curcuma longa* that protect cells from beta-amyloid insult: a drug discovery effort against Alzheimer's disease. J Nat Prod. 2002; 65(9):1227-31). It is reported to exhibit excellent anti-obesity potential (U.S. Pat. No. 8,933,121), prevents steatosis of liver (U.S. Pat. No. 9,737,502) and reduces cholesterol level in blood (U.S. Pat. No. 9,668,999). Thus, Calebin-A possesses excellent therapeutic properties which could be tapped for use in managing different disease conditions.

Calebin-A is present only in minute quantities in the rhizomes of *Curcuma* sp., hence, different synthetic methods have been developed for increasing the production of Calebin-A. Kim and Kim, Total synthesis of Calebin-A, preparation of its analogues, and their neuronal cell protectivity against beta-amyloid insult, Bioorg Med Chem Lett. 2001; 11(18):2541-3, discloses a synthetic route for the preparation of Calebin-A. U.S. Pat. No. 9,365,486 discloses a simple and scalable process for the synthesis of Calebin-A. However, the synthetic routes involve multiple stages. Hence, there exists an unmet industrial need to find a cheaper, economical and natural biotransformative route which involves a single stage conversion of curcumin/curcuminoids to calebin-A. The present invention solves the above problem by disclosing a novel, safe and reliable method for the bioconversion of curcuminoids to calebin-A using microorganisms.

The rhizomes of *Curcuma* sp. hosts many endophytic fungal species. But, the type and strain of most fungus remains yet to be identified. Further, it is unclear if the endophytic fungus, by themselves synthesize Calebin-A or would be able to catalyze the conversion of curcuminoids to calebin-A. The present invention is thus aimed at identifying the specific strain of the endophytic fungus present in the rhizomes of *Curcuma* sp. and its ability to convert curcuminoids to calebin-A.

The principle object of the invention is to disclose a method for isolation and identification of the endophytic fungus from the rhizomes of *Curcuma* sp.

It is another object of the invention to disclose a novel method for the bioconversion of curcumin to calebin-A using endophytic fungal and bacterial strains.

The invention solves the above mentioned objectives and provides further related advantages.

SUMMARY OF THE INVENTION

The present invention discloses a method for the bioconversion of curcuminoids to Calebin-A using micro-organisms. The method comprises the following steps:
i) Culturing the micro-organisms in two batches (batch 1 and batch 2) in 50 ml-500 ml volumes of suitable media and incubating at 35-37° C. with shaking at 100-120 rpm for 1 to 21 days;
ii) After 7 days of incubation addition of varying concentrations of curcuminoids to batch 1 flasks of step i) and incubating at 37° C. with 120 rpm shaking;
iii) Maintaining the batch 2 flasks of step i) without adding curcuminods at 37° C. with 120 rpm shaking;
iv) Harvesting the broth from batch 1 and batch 2 flasks of step ii) and step iii) after 24, 48, 72, 96, 120 hrs.
v) Drying the harvested sample of step iv) under vacuum and extracting using a suitable solvent;
vi) Identifying the presence of Calebin-A using HPTLC, HPLC, LC-MS and NMR.
vii) Refluxing the harvested sample of step iv) with a suitable solvent followed by separating and drying the solvent layer under vacuum;
viii) Identifying the presence of Calebin-A using HPTLC, HPLC, LC-MS and NMR.

The invention also discloses a method for the isolation and identification of endophytic fungal strain from the rhizome of *Curcuma* sp. for the bioconversion of curcuminoids to calebin, said method comprising steps of:
i) Washing the rhizomes of *Curcuma* sp., thoroughly followed by surface sterilisation using 70% ethanol for 1 minute and immersing in 0.25% mercuric chloride solution for 30 seconds to 1 minute
ii) Rinsing in sterile distilled water for 1 minute and inoculating the rhizome in a plate containing potato dextrose agar supplemented with antibiotic Tetracycline and incubated at 28±10° C. for 5 to 7 days
iii) Transferring the pure colonies on a slant and broth containing potato dextrose
iv) Preserving the fungal strains in the pure culture on PDA slant at 4 to 5° C. with proper labeling and with constant sub-culturing
v) Identifying the fungal species as *Ovatospora brasiliensis* MTCC 25236 using biochemical, microscopic and molecular methods.

The invention also discloses an inoculum containing the fungal species *Ovatospora brasiliensis* MTCC 25236, for the bioconversion of curcuminoids to calebin-A.

Other features and advantages of the present invention will become apparent from the following more detailed description, taken in conjunction with the accompanying images, which illustrate, by way of example, the principle of the invention.

DESCRIPTION OF PREFERRED EMBODIMENTS

Figure 1:
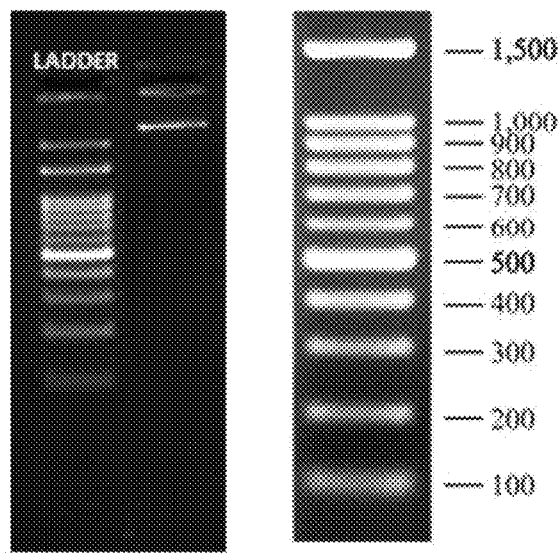
FIG. 1 is an agarose gel electrophoresis image showing the isolated DNA from endophytic fungi *Ovatospora brasiliensis* MTCC 25236.

In a preferred embodiment, the invention discloses a method for the bioconversion of curcuminoids to Calebin-A using micro-organisms, said method comprising steps of:
i) Culturing the micro-organisms in two batches (batch 1 and batch 2) in 50 ml-500 ml volumes of suitable media and incubating at 35-37° C. with shaking at 100-120 rpm for 1 to 21 days;
ii) After 7 days of incubation addition of varying concentrations of curcuminoids to batch 1 flasks of step i) and incubating at 37° C. with 120 rpm shaking;
iii) Maintaining the batch 2 flasks of step i) without adding curcuminods at 37° C. with 120 rpm shaking;
iv) Harvesting the broth from batch 1 and batch 2 flasks of step ii) and step iii) after 24, 48, 72, 96, 120 hrs.

v) Drying the harvested sample of step iv) under vacuum and extracting using a suitable solvent;

vi) Identifying the presence of Calebin-A using HPTLC, HPLC, LC-MS and NMR.

vii) Refluxing the harvested sample of step iv) with a suitable solvent followed by separating and drying the solvent layer under vacuum;

viii) Identifying the presence of Calebin-A using HPTLC, HPLC, LC-MS and NMR.

In a related embodiment, the micro-organisms are selected from the group consisting of fungal and bacterial species. In another related embodiment, the fungus preferably belongs to the genus *Chaetomium* and *Ovatospora*. In another related aspect, the fungus is most preferably *Ovatospora brasiliensis* MTCC 25236. In another related aspect, the bacterial are selected from the group comprising *Acinetobacter calcoaceticus* or *Acinetobacter johnsonii Dietzia maris, Pseudomonas putida* and *Rhodococcus ruber*. In another related aspect, the bacterial species are preferably *Acinetobacter johnsonii* and *Pseudomonas putida*. In another related aspect, the media of step i) is selected from the group comprising, but not limited to, potato dextrose broth (PDB), Sabouraud Dextrose Broth, Malt Extract Broth and Czapek Dox Broth. In another related aspect, the solvent of step v) and vii) is selected from the group comprising ethyl acetate, methanol, hexane, ethanol, acetone. In another related aspect, the solvent of step v) and vii) is preferably ethyl acetate and methanol.

In another preferred embodiment, the invention discloses a method for the isolation and identification of endophytic fungal strain for the bioconversion of curcuminoids to calebin, said method comprising steps of:

i) Washing the rhizomes of *Curcuma* sp., thoroughly followed by surface sterilization using 70% ethanol for 1 minute and immersing in 0.25% mercuric chloride solution for 30 seconds to 1 minute ii) Rinsing in sterile distilled water for 1 minute and inoculating the rhizome in a plate containing potato dextrose agar supplemented with antibiotic Tetracycline and incubated at 28±10° C. for 5 to 7 days;

iii) Transferring the pure colonies on a slant and broth containing potato dextrose iv) Preserving the fungal strains in the pure culture on potato dextrose agar (PDA) slant at 4 to 5° C. with proper labeling and with constant sub-culturing v) Identifying the fungal species using biochemical, microscopic and molecular methods.

In another related embodiment, the fungus preferably belongs to the genus *Chaetomium* and *Ovatospora*. In another related aspect, the fungus is most preferably *Ovatospora brasiliensis* MTCC 25236. In another related aspect, the *Curcuma* sp. is preferably *Curcuma caesia*.

In another preferred embodiment, the invention discloses an inoculum containing an endophytic fungal strain, isolated from the rhizomes of *Curcuma* sp., for use in the bioconversion of curcuminoids to Calebin-A. In another related embodiment, the fungus preferably belongs to the genus *Chaetomium* or *Ovatospora*. In another related aspect, the fungus is most preferably *Ovatospora brasiliensis* MTCC 25236. In another related aspect, the *Curcuma* sp. is preferably *Curcuma caesia*.

The invention is best described by the following illustrative examples:

Example 1: Isolation, Identification and Characterization of Endophytic Fungus

Isolation of Endophytic Fungi

*Curcuma caesia* rhizomes were harvested at proper time and the well grown and non infected rhizomes were selected for the isolation of endophytic fungus. The processed rhizomes were washed in running water to remove all outer sand particles and then dried with tissue paper prior to the soaking in the 70% alcohol treatment for 1 min and then in the 5.3% Sodium hypochlorite for 5 min. Finally the rhizomes were soaked in 0.25% of Mercuric chloride ($HgCl_2$) for 30 seconds and rinsed in distilled water for 1 minute and sliced both horizontally and vertically. The sliced rhizome pieces were carefully placed in the petri-dishes containing PDA medium with 0.5% w/v chloramphenicol. The Petri-dishes of inoculated rhizomes were then incubated at 28° C.-32° C. for 7 to 14 days with regular monitoring for its purity.

Screening and Identification of Endophytic Fungus

The grown culture was separated out for its pure subculture, which was subjected to the microscopic identification. The microscopic identification was done by taking the pure culture mounted on the glass slide and observed the various characters under the microscope Nikon Eclipse Ci, (Made in Japan) (Dugan, 2006). Photographic images were captured using Nikon DS Ri2 attached to a Nikon Eclipse Ci microscope. The images were processed on Nikon Basic Essential software.

Fungal DNA Extraction and Sequencing

DNA was isolated from the endophytic isolate and the quality of DNA was evaluated on 1.0% Agarose Gel. A single band of high-molecular weight DNA was observed (FIG. 1). Fragment of 18S rDNA region was amplified by PCR. The primers used are below:

```
                                        SEQ ID 1
    NS1- 5'-GTAGTCATATGCTTGTCTC-3'

SEQ ID 2
    NS4- 5'-CTTCCGTCAATTCCTTTAAG-3'
```

Figure 2:
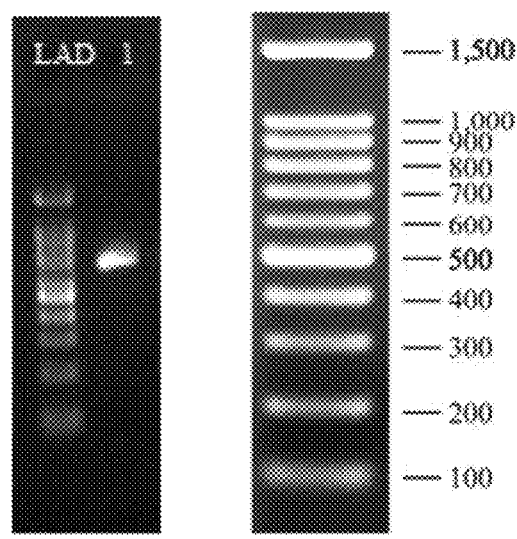
FIG. 2 is an agarose gel electrophoresis image showing the fragment of 18s rDNA amplified using polymerase chain reaction.

A single discrete PCR amplicon band of ~500 bp was observed when resolved on agarose (FIG. 2). The PCR amplicon was purified to remove contaminants. Forward and reverse DNA sequencing reaction of PCR amplicon was carried out with NS1 (5'-GTAGTCATATGCTTGTCTC-3'-SEQ ID 1) and NS4 (5'-CTTCCGTCAATTCCTTTAAG-3'-SEQ ID 2) primers using BigDye™ Terminator v3.1 Cycle sequencing kit (Applied Biosystems, Foster City, Calif.) on ABI 3730XL Genetic Analyzer (Applied Biosystems). Consensus sequence of the PCR amplicon was generated from forward and reverse sequence data using aligner software. The 18S rDNA region sequence was used to carry out BLAST with the database of NCBI Genbank. Based on maximum identity score first ten sequences were selected and aligned using multiple alignment software program Clustal W. Distance matrix was generated and the phylogenetic tree was constructed using MEGA 7.

Results

The fungal 18S rDNA was sequenced and the sequence information (SEQ ID 3) was obtained as below:

```
5' AGGAAGTAAAAGTCGTAACAAGGTCTCCGTTGGTGAACCAGCGGAG

GGATCATTAAAGAGTTGCAAAACTCCCTAAACCATTGTGAACCTACCTT

CAACCGTTGCTTCGGCGGGTTGGCACCGGGTCTCCCGGCGCCCCCGGCC

CCCTCGCGGGGCGGCCCGCCGGAGGTACCTAACTCTTGAACATTGTATG
```

-continued
```
GCCTCTCTGAGTCTTCTGTACTGAATAAGTCAAAACTTTCAACAACGGA

TCTCTTGGTTCTGGCATCGATGAAGAACGCAGCGAAATGCGATAAGTAA

TGTGAATTGCAGAATTCAGTGAATCATCGAATCTTTGAACGCACATTGC

GCCCGCCAGTATTCTGGCGGGCATGCCTGTTCGAGCGTCATTTCAACCA

TCAAGCCCCGGGCTTGTGTTGGGGACCTGCGGCTGCCGCAGGCCCTGAA
```

-continued
```
ATGCAGTGGCGGGCTCGCTGTCACACCGAGCGTAGTAGCATTATCTCGC

TCTGGGCGTGCTGCGTGTCCCGGCCGTAAAACGACCTTACACCCAAGGT

TGACCTCGGATCAGGTAGGAAGACCCGCTGAACTTAAGCATATCAA 3'
```

Figure 3:
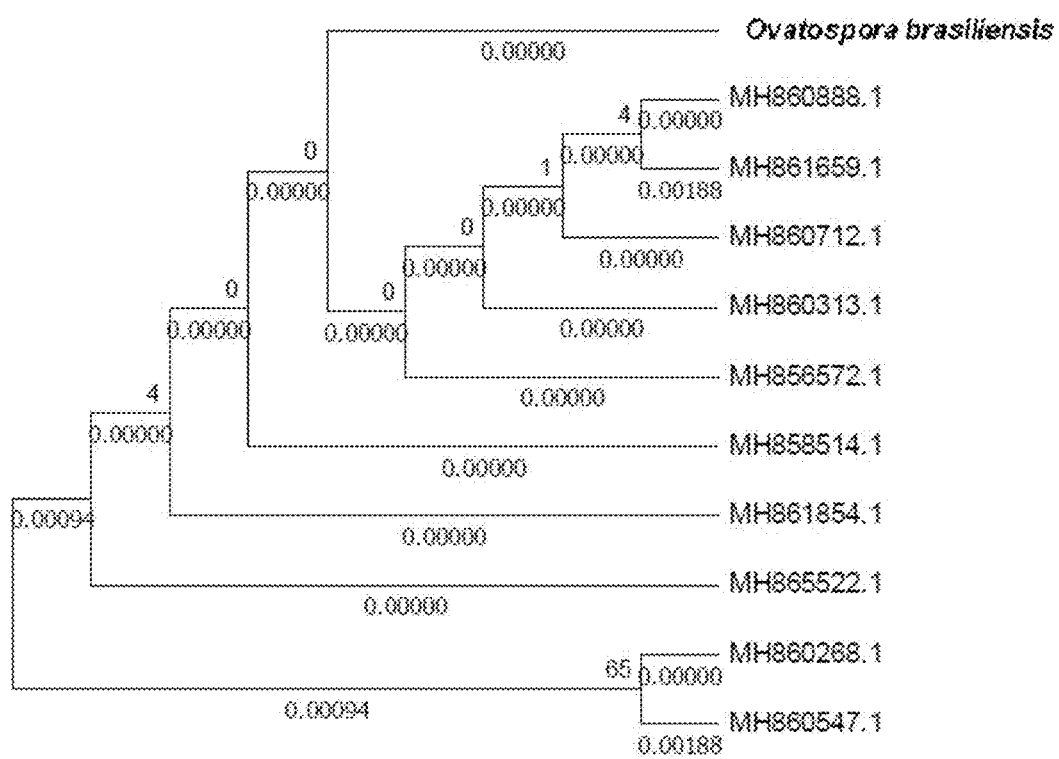
FIG. 3 represents the Phylogenetic Tree for the identification of *Ovatospora brasiliensis* MTCC 25236 derived through Molecular Phylogenetic analysis by Maximum Likelihood method.

The endophytic fungus which was labelled as Endophytic Fungus EPE 10 showed high similarity with *Ovatospora brasiliensis* based on nucleotide homology (Table 1) and phylogenetic analysis (FIG. 3 and Table 2).

TABLE 1

Alignment view using combination of NCBI GenBank - Distribution of 10 Blast Hits on the Query Sequence

| Description | Max score | Total score | Query cover | E value | Ident | Accession |
| --- | --- | --- | --- | --- | --- | --- |
| *Ovatospora brasiliensis* strain CBS 122.65 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 1075 | 1075 | 100% | 0 | 100.00% | MH858514.1 |
| *Chaetomium fuscum* strain CBS 140.50 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 1068 | 1068 | 99% | 0 | 99.83% | MH856572.1 |
| *Ovatospora mollicella* strain CBS 101.85 small subunit ribosomal RNA gene, partial sequence; internal transcribed spacer 1, 5.8S ribosomal RNA gene, and internal transcribed spacer 2, complete sequence; and large subunit ribosomal RNA gene partial sequence | 1064 | 1064 | 98% | 0 | 100.00% | MH861854.1 |
| *Ovatospora brasiliensis* strain CBS 728.71 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 1051 | 1051 | 97% | 0 | 100.00% | MH860313.1 |
| *Ovatospora brasiliensis* strain CBS 578.71 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 1051 | 1051 | 98% | 0 | 99.83% | MH860268.1 |
| *Ovatospora brasiliensis* strain CBS 391.73 small subunit ribosomal RNA gene, partial sequence; internal transcribed spacer 1, 5.8S ribosomal RNA gene, and internal | 1050 | 1050 | 97% | 0 | 100.00% | MH860712.1 |

TABLE 1-continued

Alignment view using combination of NCBI GenBank - Distribution of 10 Blast Hits on the Query Sequence

| Description | Max score | Total score | Query cover | E value | Ident | Accession |
|---|---|---|---|---|---|---|
| transcribed spacer 2, complete sequence; and large subunit ribosomal RNA gene, partial sequence | | | | | | |
| *Ovatospora brasiliensis* strain CBS 690.74 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 1046 | 1046 | 97% | 0 | 100.00% | MH860888.1 |
| *Ovatospora brasiliensis* strain CBS 507.72 small subunit ribosomal RNA gene, partial sequence; internal transcribed spacer 1. 5.8S ribosomal RNA gene, and internal transcribed spacer 2, complete sequence; and large subunit ribosomal RNA gene, partial sequence | 1046 | 1046 | 98% | 0 | 99.65% | MH860547.1 |
| *Ovatospora mollicella* strain CBS 583.83 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 1044 | 1044 | 97% | 0 | 99.82% | MH861659.1 |
| *Ovatospora brasiliensis* strain CBS 130174 small subunit ribosomal RNA gene, partial sequence; internal transcribed spacer 1 and 5.8S ribosomal RNA gene, complete sequence; and internal transcribed spacer 2, partial sequence | 996 | 996 | 92% | 0 | 100.00% | MH865522.1 |

TABLE 2

Estimates of Evolutionary Divergence between Sequences using phylogenetic analysis

| | | | | | | | | | | | |
|---|---|---|---|---|---|---|---|---|---|---|---|
| Endophytic Fungus EPE 10 | | 0.000 | 0.000 | 0.000 | 0.000 | 0.002 | 0.000 | 0.000 | 0.003 | 0.002 | 0.000 |
| MH858514.1 | 0.000 | | 0.000 | 0.000 | 0.000 | 0.002 | 0.000 | 0.000 | 0.003 | 0.002 | 0.000 |
| MH856572.1 | 0.000 | 0.000 | | 0.000 | 0.000 | 0.002 | 0.000 | 0.000 | 0.003 | 0.002 | 0.000 |
| MH861854.1 | 0.000 | 0.000 | 0.000 | | 0.000 | 0.002 | 0.000 | 0.000 | 0.003 | 0.002 | 0.000 |
| MH860313.1 | 0.000 | 0.000 | 0.000 | 0.000 | | 0.002 | 0.000 | 0.000 | 0.003 | 0.002 | 0.000 |
| MH860268.1 | 0.002 | 0.002 | 0.002 | 0.002 | 0.002 | | 0.002 | 0.002 | 0.002 | 0.003 | 0.002 |
| MH860712.1 | 0.000 | 0.000 | 0.000 | 0.000 | 0.000 | 0.002 | | 0.000 | 0.003 | 0.002 | 0.000 |
| MH860888.1 | 0.000 | 0.000 | 0.000 | 0.000 | 0.000 | 0.002 | 0.000 | | 0.003 | 0.002 | 0.000 |
| MH860547.1 | 0.004 | 0.004 | 0.004 | 0.004 | 0.004 | 0.002 | 0.004 | 0.004 | | 0.003 | 0.003 |
| MH861659.1 | 0.002 | 0.002 | 0.002 | 0.002 | 0.002 | 0.004 | 0.002 | 0.002 | 0.006 | | 0.002 |
| MH865522.1 | 0.000 | 0.000 | 0.000 | 0.000 | 0.000 | 0.000 | 0.000 | 0.000 | 0.004 | 0.002 | |

Figure 4:
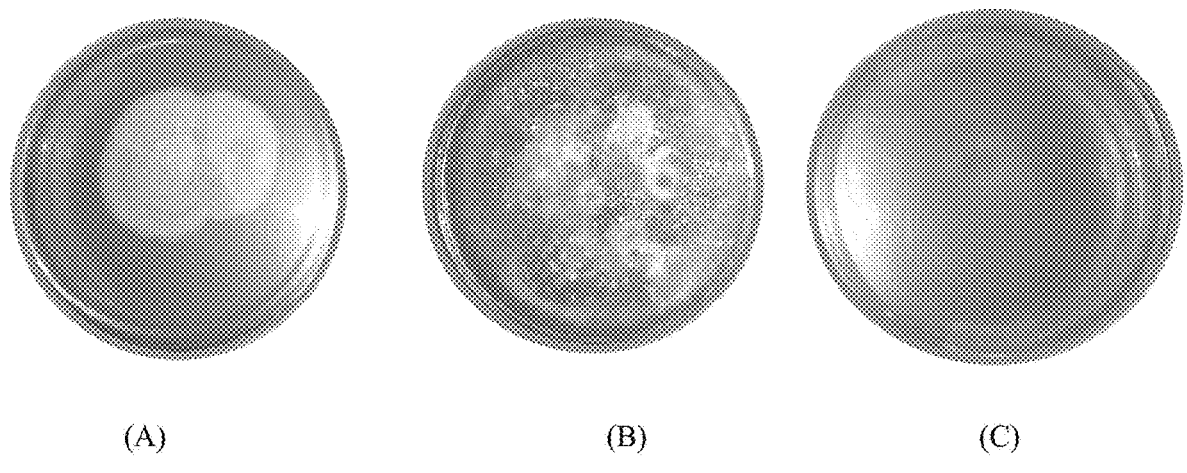
FIG. 4 shows the Agar plate culture of the isolated fungus *Ovatospora brasiliensis* MTCC 25236 from 7 days to 21 days of growth. Image a) shows Growth after 7 days, image b) shows growth after 21 days and image c) is a blank plate with media which serves as control.
Figure 5:
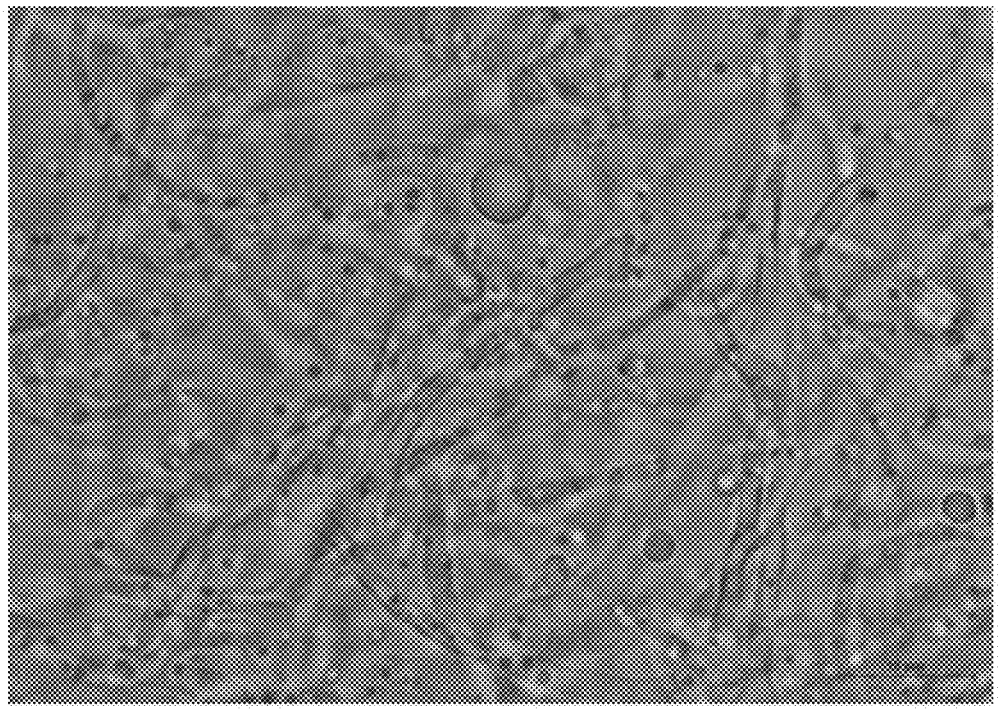
FIG. 5 is the microscopic image of *Ovatospora brasiliensis* MTCC 25236, showing the hyphae as septate filaments.

This isolated endophytic fungus EPE-10 was deposited in the Microbial Type Culture Collection and Gene Bank and was assigned the strain number MTCC 25236. The colony of *Ovatospora brasiliensis* MTCC 25236 was grayish white with a cottony texture, having black dots on the surface (FIG. 4). The hyphae were septate with pale brown color. Perithecia was oval brown to black color and surrounded by long helical filamentous appendages. The ascospores were dark brown, oval shape with single cell of no septum (FIG. 5).

Figure 6:
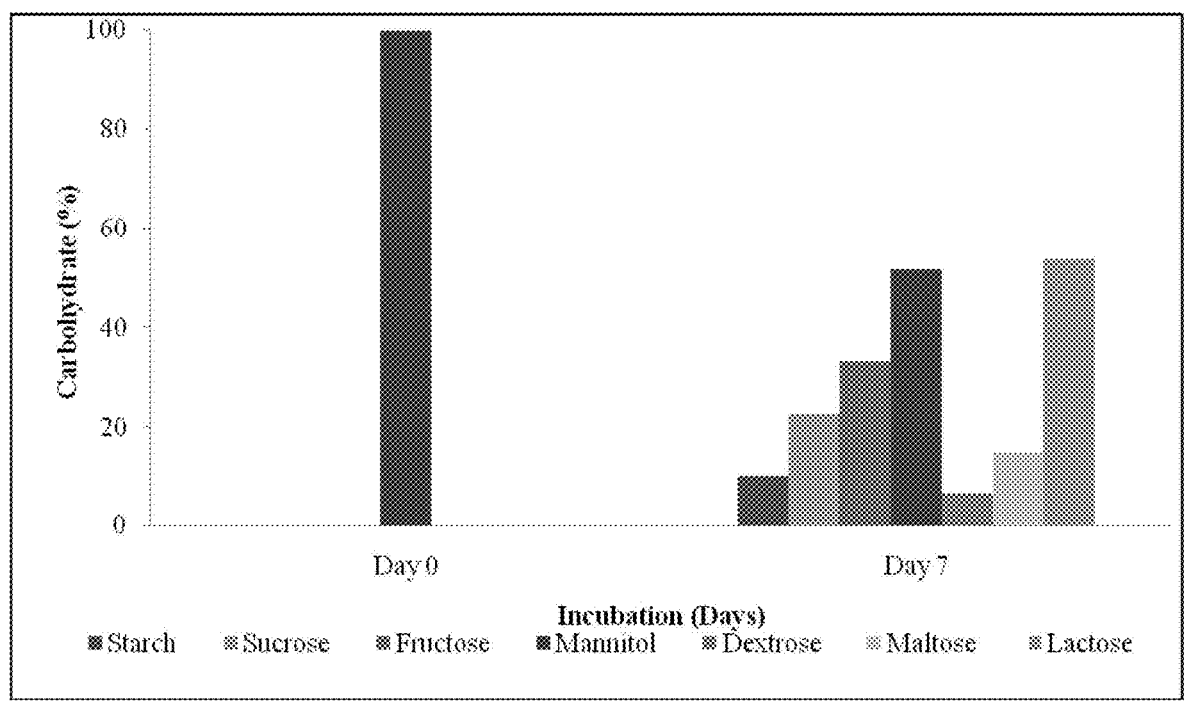
FIG. 6 is the graphical representation showing Carbohydrate utilization by *Ovatospora brasiliensis* MTCC 25236.

The biochemical characterization was done for *Ovatospora brasiliensis* MTCC 25236 and it gave positive results for catalase test and Esculin hydrolysis (Table 3). The fungus also utilized different carbohydrates for its growth (Table 4, FIG. 6). *Ovatospora brasiliensis* is also known as *Chaetomium brasiliense (Ovatospora brasiliensis* (Bat. & Pontual) X. Wei Wang & Samson, Studies in Mycology 84: 207 (2016); http://www.mycobank.org/BioloMICSDetails.aspx?Rec=556121).

TABLE 3

Biochemical characterization of *Ovatospora brasiliensis* MTCC 25236

| S. No. | Test | *O. brasiliensis* MTCC 25236 |
|---|---|---|
| 1 | Catalase | + |
| 2 | Indole | − |
| 3 | Methyl Red | − |
| 4 | Voges Proskauers | − |
| 5 | Citrate | − |
| 6 | Esculin hydrolysis | + |

+ Positive,
− Negative

TABLE 4

Carbohydrate utilization by Endophytic Fungi (EPE-10) for the growth

| | | *O. brasiliensis*, MTCC 25236 | |
|---|---|---|---|
| S. No. | Test | Growth | Color change red to Yellow |
| 1 | Starch | +++ | ++ |
| 2 | Dextrose | +++ | ++ |
| 3 | Lactose | +++ | − |
| 4 | Fructose | +++ | + |
| 5 | Mannitol | + | − |
| 6 | Sucrose | +++ | ++ |
| 7 | Maltose | +++ | − |

+ Mild reaction,
++ Medium reaction;
+++ Complete reaction

Example 2: Bioconversion of Curcuminoids to Calebin-A

Methods

The identified *O. brasiliensis*. MTCC 25236 was grown in PDB for minimum 7 days to maximum 21 days in 500 ml volumes of suitable media at optimal incubation conditions. 1%-5% of 72 hrs grown culture was added to 500 ml of PDB and incubated at 25-35° C. with 120 rpm agitation for 5-21 days. *Acinetobacter johnsonii* NCIMB 9871 or *Pseudomonas putida* NCIMB 10007 were purchased from NCIMB Ltd, Ferguson Building, Craibstone Estate, Bucksburn, Aberdeen, AB21 9YA. *Pseudomonas putida, Acinetobacter johnsonii* were grown in a media containing bacteriological peptone 17 g/L, soya peptone 3 g/L, dextrose 2.5 g/L, $MnSO_4$ 0.1 g/L, $MgSO_4$ 0.1 g/L, $CaCl_2$) 0.1 g/L, $K_2HPO_4$ 2 g/L, $KH_2PO_4$ 1 g/L, and pH was adjusted to 6.5. The media was sterilized for 15 min at 121° C. A single isolated colony of *Pseudomonas putida* and *Acinetobacter johnsonii* were inoculated into flask containing the media. Further, the flasks were incubated at 37° C. for 72 h. At different time intervals 24 h, 48 h, 72 h and 10 ml of broth was collected and checked for optical density (OD), total reducing sugar and pH.

Curcuminoids or commercially available Curcumin C3 Complex® (Registered™ of Sabinsa Corporation, USA) ranging from 0.5 mg to 50 mg was added after 7 days and further incubated at 25-35° C. with 120 rpm agitation. The flasks were harvested every 24, 48, 72, 96, 120 hrs, and centrifuged to separate the supernatant. The supernatant was then dried under vacuum and the components were extracted using ethyl acetate and methanol successively. The presence of Calebin-A in the extracts was identified and quantified using HP-TLC, HPLC and LCMS.

High Performance Thin Layer Chromatography (HP-TLC)

For the analysis, pre coated 60 F254 silica gel plates were used. Plant extract using ethyl acetate and methanol was applied with a 100 µl Linomat syringe using a semi-automatic Linomat V applicator (Camag, Muttenz, Switzerland). 2 µl of each sample was loaded on the plates and developed using Chloroform: Methanol (98:2). Using scanner 3 (Camag) the plate was scanned at 280 nm with deuterium illumination. The images were captured on Camag reprostar 3 with win CATS software (ver. 1.4.3.6336). Fungal extracts of ethyl acetate and methanol were concentrated and taken as semi-solid paste from 500 ml culture and the yield were calculated. The known concentrated of the sample were dissolved in the respective solvent for the HPTLC analysis.

High Performance-Liquid Chromatography (HPLC)

The sample was analyzed by Shimadzu Class Vp series using a Zorbax C18 column (250×4.6 mm, 5µ particle size), binary gradient pump (LC10 ATVp), a DAD detector (SPD-M10A Vp), a system controller (SCL-10A Vp), and a Rheodyne injector with 20 µl sample loop. The mobile phase was 0.6 g Citric acid (AR grade) and 400 mL of tetrahydrofuran (HPLC grade) in 1000 ml milli-Q water was filtered through 0.2µ membrane filter before use and pumped from the solvent reservoir at a flow rate of 1.0 ml/minutes, which yielded column backup, the pressure of 160-170 kgf/cm2 the column was maintained at 27° C. syringe volume of 20 µl of respective samples were injected. Standards of 50 mg of Curcuminoids and Calebin-A were weighed accurately and dissolve with 80 mL of Tetrahydrofuran and make up to 100 ml solution in volumetric flask. Pipette out 5 mL of stock solution of standards respectively and make up to 50 mL with the mobile phase. The sample of 1 gram dissolved with Tetrahydrofuran and make up to 100 ml solution in volumetric flask. From the stock solution of sample 5 mL taken for analysis by diluting it in 50 mL of mobile phase solution.

Results

Figure 7:
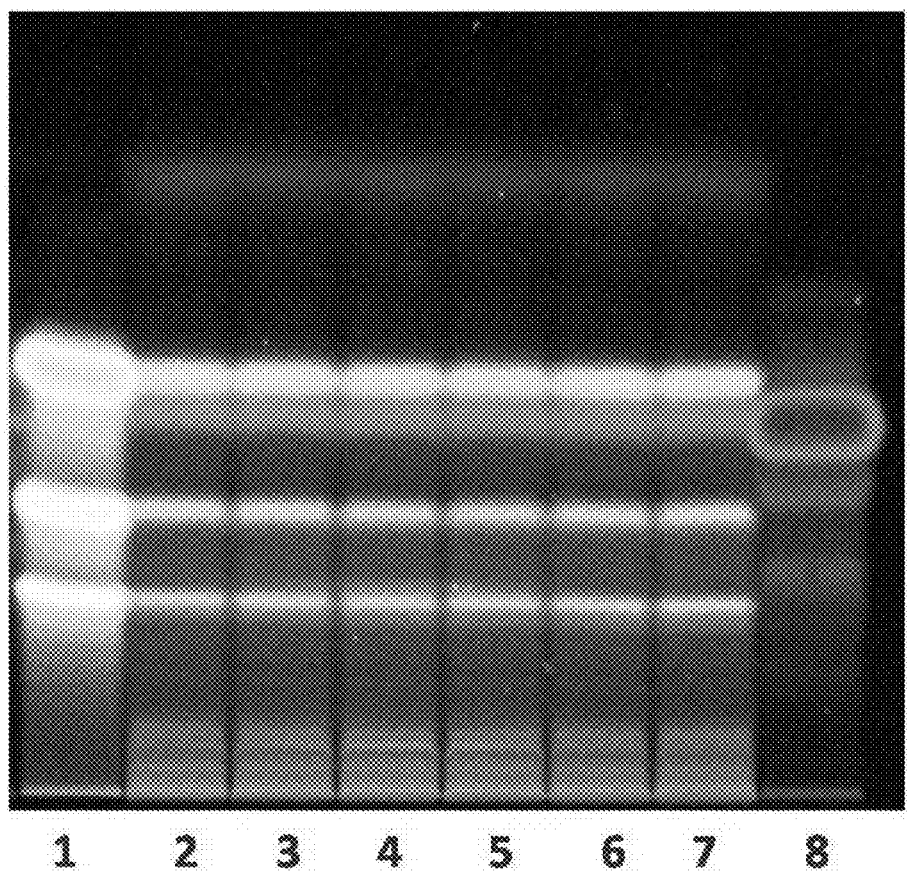
FIG. 7 shows the HPTLC fingerprint of the *Ovatospora brasiliensis* MTCC 25236 ethyl acetate extract, which shows the conversion band of Calebin-A at 366 NM, Track details: Track 1: C3 complex; Track 2-6, ethyl acetate extract of *Ovatospora brasiliensis* MTCC 25236 and Track 8-Calebin-A standard.
Figure 8:
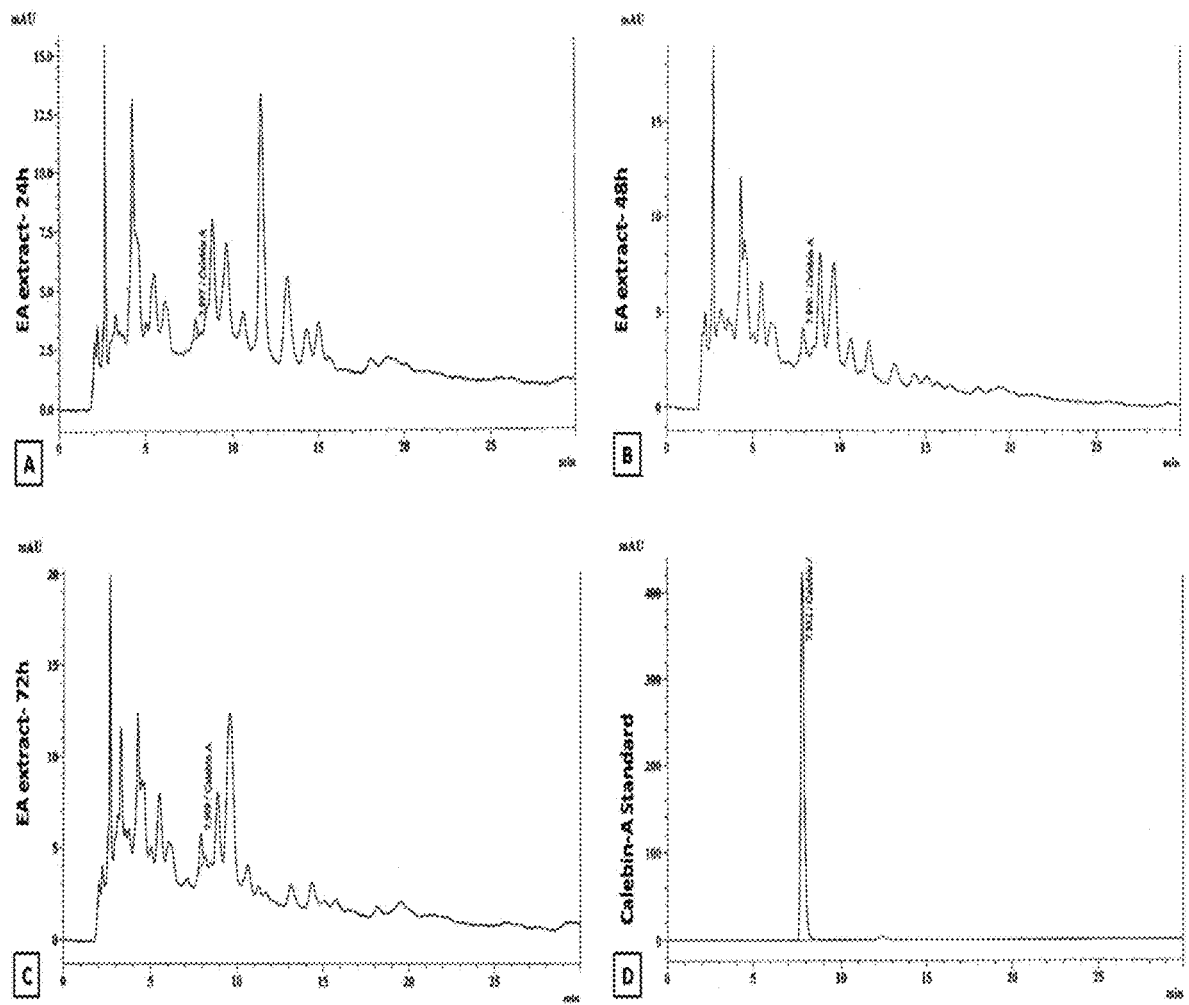
FIG. 8 shows the HPLC fingerprint of the ethyl acetate extract of *Ovatospora brasiliensis* MTCC 25236 at different growth intervals, A. extracted at 24 hours of growth; B. at 48 hours; C. 72 hours; D. Calebin-A standard. The chromatogram shows the presence of Calebin-A from the 24 hours of growth after adding Curcumin in the broth. Peaks are matching at the RT 7.8 in 30 minutes run.
Figure 9:
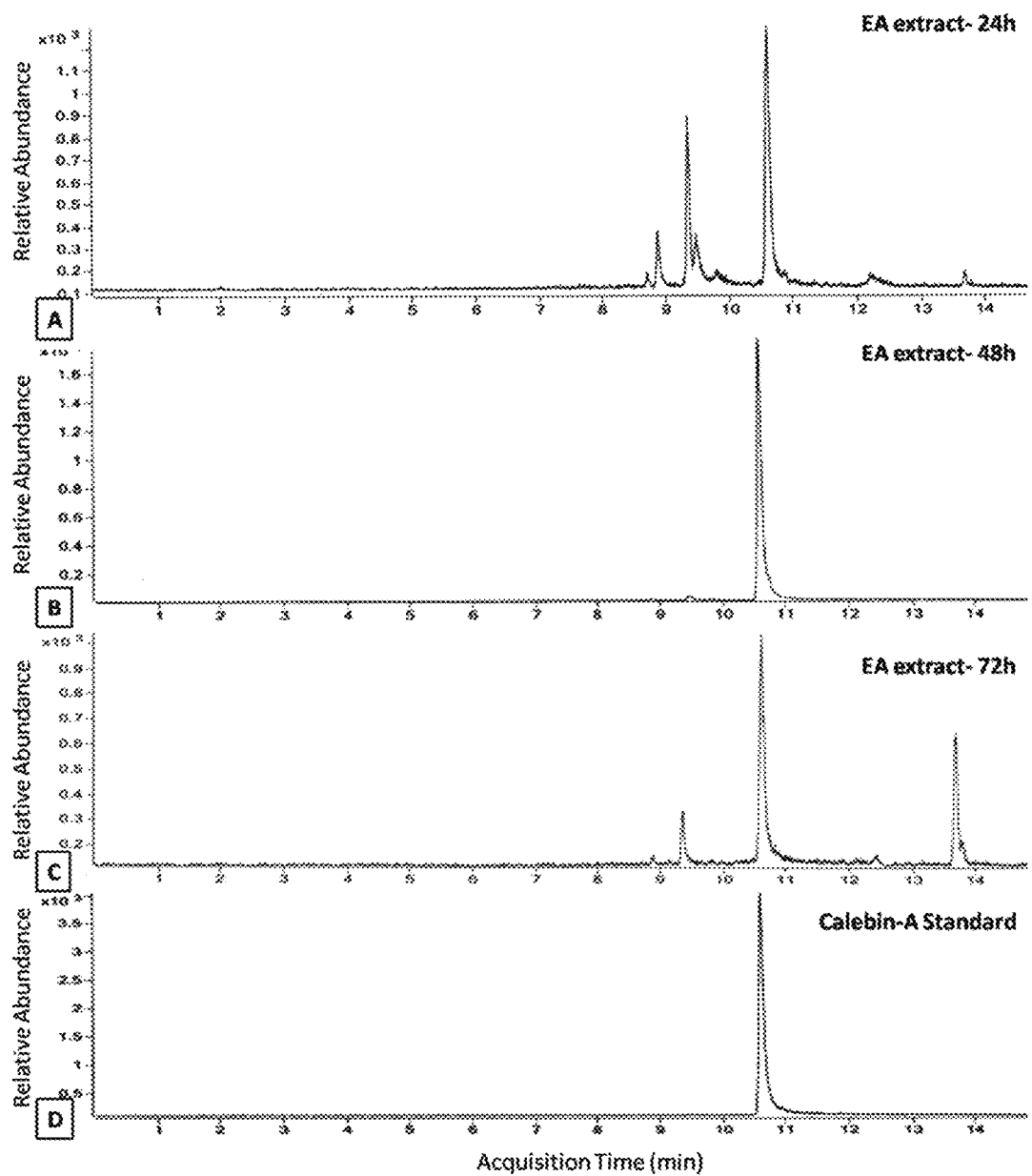
FIG. 9 shows the LC-MS Chromatogram of the ethyl acetate extract of *Ovatospora brasiliensis* EPE-10. MTCC 25236 showed the similar peak to the Calebin-A at the RT 10.55. The LCMS data more prominent in the extracts at the range of 24 hours to 72 hours culture of Curcumin added to *Ovatospora brasiliensis* EPE-10, MTCC 25236.

The conversion of curcumin into Calebin-A was more compare to the control endophytic fungus, even though the endophytic fungus itself produced minor amount of Calebin-A (which was detected through HPLC, not in HPTLC). The conversion rate was higher when the curcumin added in the medium after the three days of the inoculation of culture. The HPTLC results showed the similar band to the Calebin-A standard at the same Rf (FIG. 7). The broth was added with the C3 complex [which contains Demethoxycurcumin (DMC) and Bisdemethoxycurcumin (BDMC) along with the Curcumin]. The chromatogram showed that the presence of the Calebin-A band in the C3 complex added culture compare to the control culture (without C3 complex). This indicated that the *Ovatospora brasiliensis* EPE-10, MTCC 25236 was able to convert the curcumin into Calebin-A in the suitable growth time and suitable conditions provided. HPLC chromatogram supported the data that the *Ovatospora brasiliensis* EPE-10, MTCC 25236 converting the curcumin into Calebin-A maximum at the range of 48 to 72 hours (FIG. 8). The analysis done against with the control sample and curcumin added sample suggested that the culture was able to produce the calebin-A by its own providing the suitable environmental condition and maintain the same anaerobic condition for endophytic nature. The chromatogram of HPLC significantly matched with the standard Calebin-A at the RT of 7.8, the following chromatogram comparing the HPLC peak against the standard (FIG. 8). LCMS analysis suggested that the higher level of detection of Calebin-A in the 48 hours to 72 hours range (FIG. 9). In summary, the endophytic fungus, isolated from the *Curcuma caesia* rhizome, has the potency in converting the Calebin-A by using the Curcumin as the major substrate.

Figure 10:
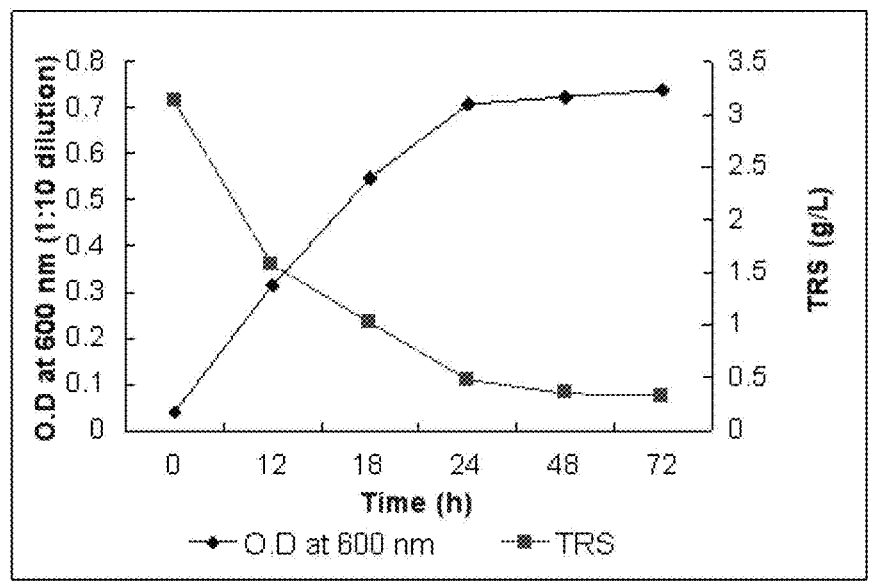
FIG. 10 is the graphical representation of growth curve of bacterial strain *Pseudomonas putida* grown in PSD medium (bacteriological peptone 17 g/L, soya peptone 3 g/L, dextrose 2.5 g/L, $MnSO_4$ 0.1 g/L, $MgSO_4$ 0.1 g/L, $CaCl_2$ 0.1 g/L, $K_2HPO_4$ 2 g/L, $KH_2PO_4$ 1 g/L, pH 6.5±0.2)
Figure 11:
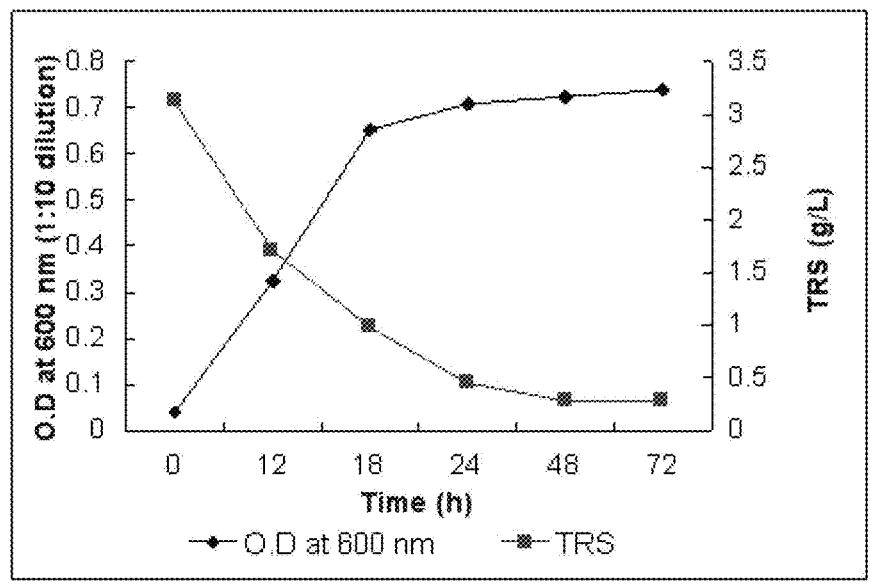
FIG. 11 is the graphical representation of growth curve of bacterial strain *Acinetobacter johnsonii* grown in PSD medium (bacteriological peptone 17 g/L, soya peptone 3 g/L, dextrose 2.5 g/L, $MnSO_4$ 0.1 g/L, $MgSO_4$ 0.1 g/L, $CaCl_2$ 0.1 g/L, $K_2HPO_4$ 2 g/L, $KH_2PO_4$ 1 g/L, pH 6.5±0.2)
Figure 12:
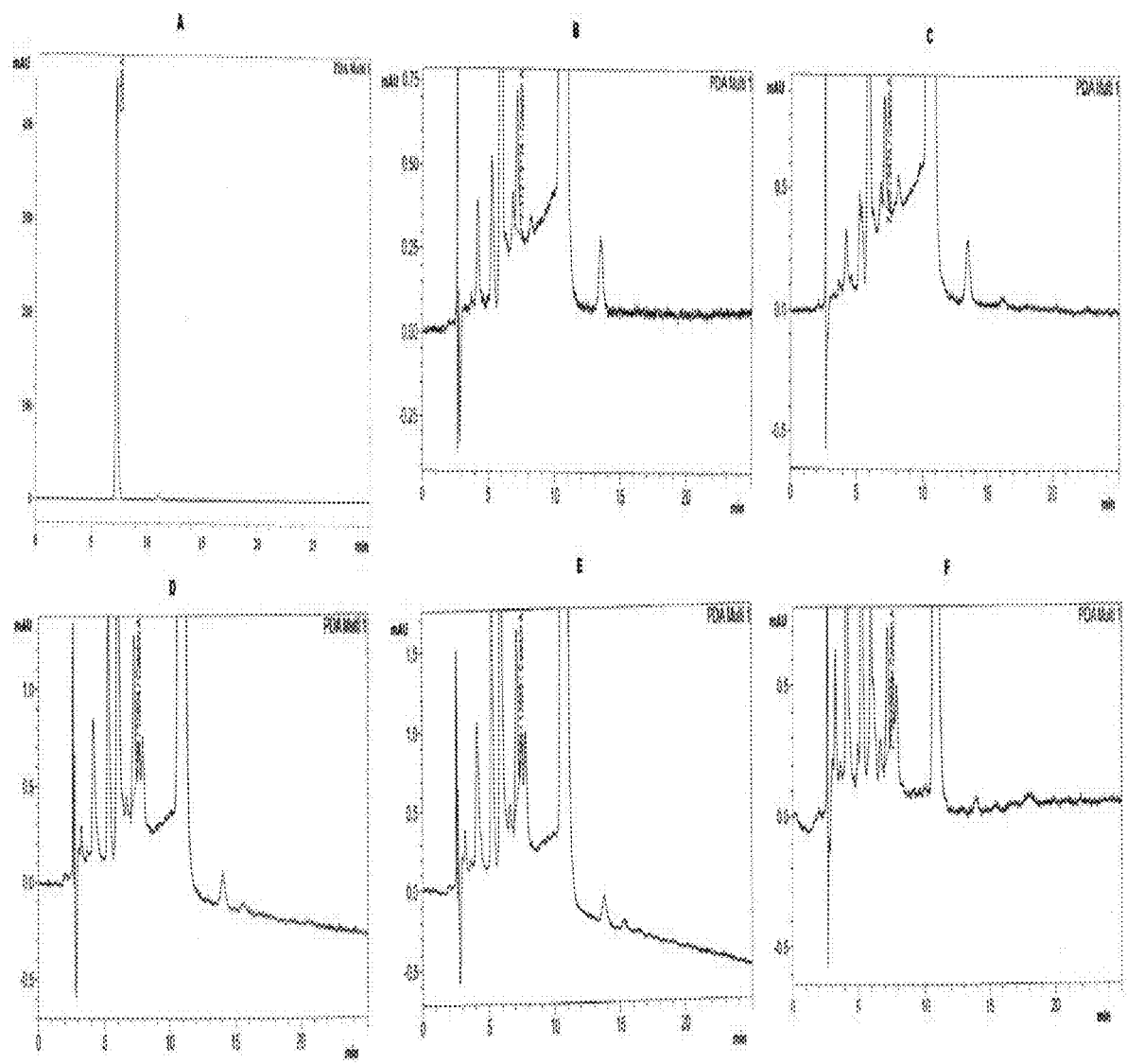
FIG. 12 shows the results of HPLC analysis showing the production of Calebin-A from curcuminoids by *Acinetobacter johnsonii* at different time intervals (A) Calebin-A standard (B) 24 m h sample (C) 48 h sample (D) 72 h sample (E) 96 h sample and (F) 120 h sample.
Figure 13:
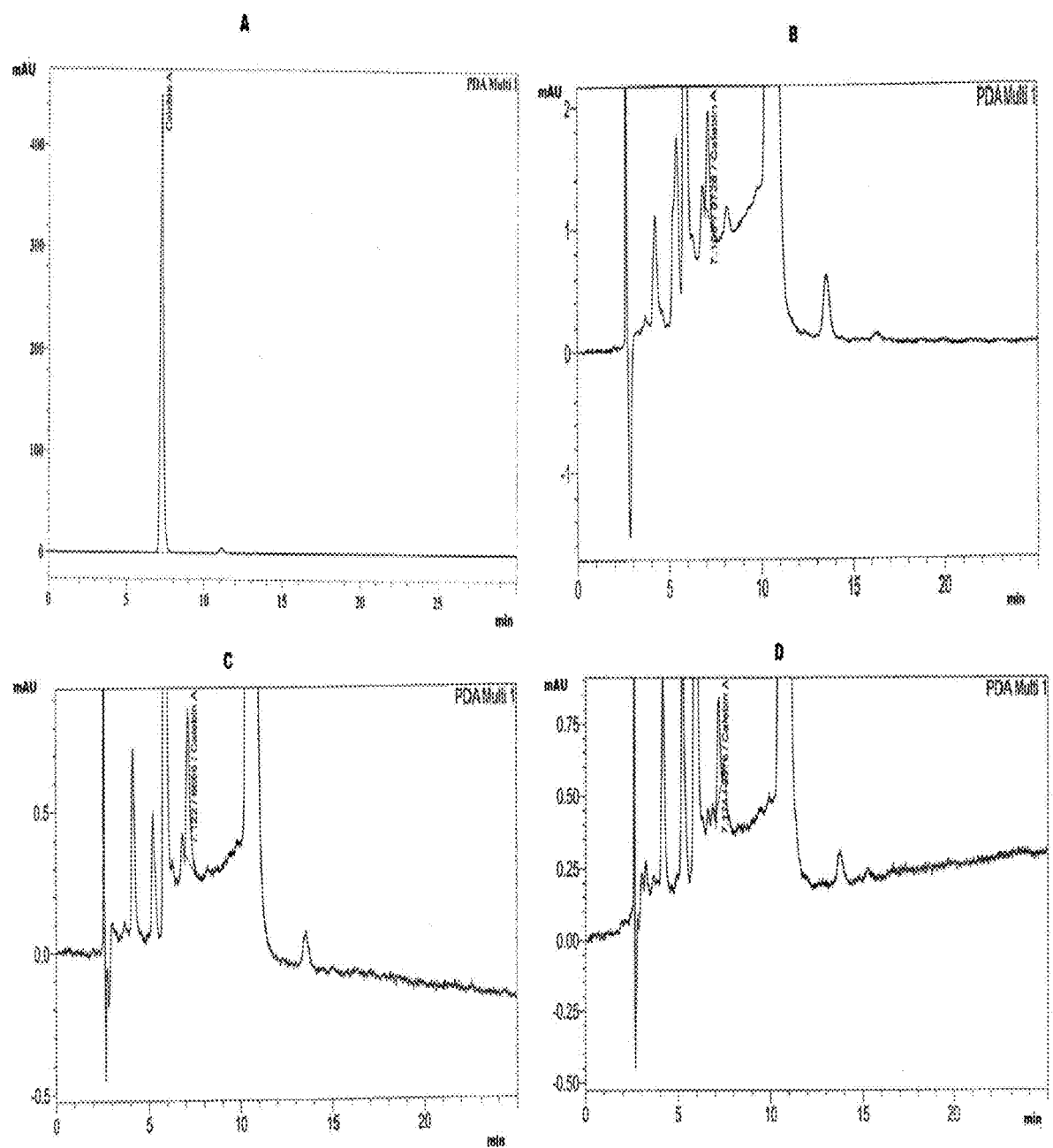
FIG. 13 shows the results of HPLC analysis showing the production of Calebin-A from curcuminoids by *Pseudomonas putida*, at different time intervals (A) Calebin-A standard (B) 24 m h sample (C) 48 h sample (D) 72 h sample (E) 96 h sample and (F) 120 h sample.

Similarly, Calebin-A was also produced from curcuminoids by bacterial species *Pseudomonas putida* NCIMB 10007 and *Acinetobacter johnsonii* NCIMB 9871. The bacterial species were cultured in suitable growth media (FIGS. 10 and 11). The same method mentioned above was performed for the bioconversion of curcuminoids to calein-A. Calebin-A was detected using HPLC (FIGS. 12 and 13), indicating that both the bacterial species, *Pseudomonas putida* NCIMB 10007 and *Acinetobacter johnsonii* NCIMB 9871, effectively converted curcuminoids to calebin-A.

While the invention has been described with reference to a preferred embodiment, it is to be clearly understood by those skilled in the art that the invention is not limited thereto. Rather, the scope of the invention is to be interpreted only in conjunction with the appended claims.

SEQUENCE LISTING

FORWARD PRIMER - NS1
SEQ ID 1
5'-GTAGTCATATGCTTGTCTC-3'

REVERSE PRIMER - NS4
SEQ ID 2
5'-CTTCCGTCAATTCCTTTAAG-3'

18s rDNA
SEQ ID 3
5'AGGAAGTAAAAGTCGTAACAAGGTCTCCGTTGGTGAACCAGCGGAGGG
ATCATTAAAGAGTTGCAAAACTCCCTAAACCATTGTGAACCTACCTTCAA
CCGTTGCTTCGGCGGGTTGGCACCGGGTCTCCCGGCGCCCCGGCCCCCT
CGCGGGGCGGCCCGCCGGAGGTACCTAACTCTTGAACATTGTATGGCCTC
TCTGAGTCTTCTGTACTGAATAAGTCAAAACTTTCAACAACGGATCTCTT
GGTTCTGGCATCGATGAAGAACGCAGCGAAATGCGATAAGTAATGTGAAT
TGCAGAATTCAGTGAATCATCGAATCTTTGAACGCACATTGCGCCCGCCA
GTATTCTGGCGGGCATGCCTGTTCGAGCGTCATTTCAACCATCAAGCCCC
GGGCTTGTGTTGGGGACCTGCGGCTGCCGCAGGCCCTGAAATGCAGTGGC
GGGCTCGCTGTCACACCGAGCGTAGTAGCATTATCTCGCTCTGGGCGTGC
TGCGTGTCCCGGCCGTAAAACGACCTTACACCCAAGGTTGACCTCGGATC
AGGTAGGAAGACCCGCTGAACTTAAGCATATCAA 3'

ASCII text file name: Microbial_bioconversion_Sequence_listing_ST25
Date Created: 19 Feb. 2019
Size: 1,827 bytes

We claim:

1. A method for the bioconversion of curcuminoids to Calebin-A using fungal or bacterial species, said method comprising steps of:
   i. culturing the fungal or bacterial species in main two batches (flasks containing batch 1 and flasks containing batch 2) in 50 ml-500 ml volumes of suitable media and incubating at 35-37° C. with shaking at 100-120 rpm for 1 to 21 days;
   ii. on the 7$^{th}$ day of incubation, adding varying concentrations of curcuminoids to batch 1 flasks of step i) and incubating at 37° C. with 120 rpm shaking;
   iii. maintaining the batch 2 flasks of step i) without adding curcuminoids at 37° C. with 120 rpm shaking;
   iv. harvesting media from batch 1 and batch 2 flasks of step ii) and step iii) after 24, 48, 72, 96, 120 hrs;
   v. drying the harvested media of step iv) under vacuum and extracting using a suitable solvent;
   vi. identifying the presence of Calebin-A using HPLC (high performance liquid chromatography), LC-MS (liquid chromatography-mass spectrometry) and NMR (nuclear magnetic resonance);
   vii. refluxing the harvested media of step iv) with a suitable solvent followed by separating and drying the solvent layer under vacuum; and
   viii. identifying the presence of Calebin-A using HPTLC, HPLC, LC-MS and NMR, wherein the fungal species is *Ovatospora brasiliensis* MTCC 25236, and the bacterial species is *Acinetobacter johnsonii* NCIMB 9871 or *Pseudomonas putida* NCIMB 10007.

2. The method as in claim 1, wherein the media of step i) is selected from the group consisting of potato dextrose broth (PDB), Sabouraud Dextrose Broth, Malt Extract Broth, and Czapek Dox Broth.

3. The method as in claim 1, wherein the solvent of step v) and vii) is selected from the group consisting of ethyl acetate, methanol, hexane, ethanol, and acetone.

4. The method as in claim 1, wherein the solvent of step v) and vii) is ethyl acetate and methanol.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Forward Primer NS1

<400> SEQUENCE: 1
gtagtcatat gcttgtctc                                          19

<210> SEQ ID NO 2
<211> LENGTH: 20
<212> TYPE: DNA
<213> ORGANISM: Artificial Sequence
<220> FEATURE:
<223> OTHER INFORMATION: Reverse Primer NS4

<400> SEQUENCE: 2
cttccgtcaa ttcctttaag                                         20

<210> SEQ ID NO 3
<211> LENGTH: 582
<212> TYPE: DNA
<213> ORGANISM: Ovatospora brasiliensis MTCC 25236

<400> SEQUENCE: 3
aggaagtaaa agtcgtaaca aggtctccgt tggtgaacca gcggagggat cattaaagag    60
ttgcaaaact ccctaaacca ttgtgaacct accttcaacc gttgcttcgg cgggttggca   120

-continued

| | | | | | | |
|---|---|---|---|---|---|---|
| ccgggtctcc | cggcgccccc | ggcccctcg | cggggcggcc | cgccggaggt | acctaactct | 180 |
| tgaacattgt | atggcctctc | tgagtcttct | gtactgaata | agtcaaaact | ttcaacaacg | 240 |
| gatctcttgg | ttctggcatc | gatgaagaac | gcagcgaaat | gcgataagta | atgtgaattg | 300 |
| cagaattcag | tgaatcatcg | aatctttgaa | cgcacattgc | gcccgccagt | attctggcgg | 360 |
| gcatgcctgt | tcgagcgtca | tttcaaccat | caagcccgg | gcttgtgttg | gggacctgcg | 420 |
| gctgccgcag | gccctgaaat | gcagtggcgg | gctcgctgtc | acaccgagcg | tagtagcatt | 480 |
| atctcgctct | gggcgtgctg | cgtgtcccgg | ccgtaaaacg | accttacacc | caaggttgac | 540 |
| ctcggatcag | gtaggaagac | ccgctgaact | taagcatatc | aa | | 582 |